(12) United States Patent
Nunez et al.

(10) Patent No.: US 11,324,961 B2
(45) Date of Patent: May 10, 2022

(54) APPARATUS AND METHOD FOR PROVIDING HYPERTHERMIA THERAPY

(71) Applicants: Albert Nunez, Oviedo, FL (US); Eric Miller, Coral Gables, FL (US); Gary Minker, Coral Gables, FL (US); Alex Nunez, Coral Gables, FL (US); Anthony Nunez, Coral Gables, FL (US); Jorge Barrera, Coral Gables, FL (US); Jose Antonio Collazo, Coral Gables, FL (US)

(72) Inventors: Albert Nunez, Oviedo, FL (US); Eric Miller, Coral Gables, FL (US); Gary Minker, Coral Gables, FL (US); Alex Nunez, Coral Gables, FL (US); Anthony Nunez, Coral Gables, FL (US); Jorge Barrera, Coral Gables, FL (US); Jose Antonio Collazo, Coral Gables, FL (US)

(*) Notice: Subject to any disclaimer, the term of this patent is extended or adjusted under 35 U.S.C. 154(b) by 502 days.

(21) Appl. No.: 14/851,928

(22) Filed: Sep. 11, 2015

(65) Prior Publication Data

US 2016/0074668 A1    Mar. 17, 2016

Related U.S. Application Data

(60) Provisional application No. 62/049,802, filed on Sep. 12, 2014.

(51) Int. Cl.
*A61N 1/40* (2006.01)
*A61N 5/04* (2006.01)
*A61N 5/02* (2006.01)

(52) U.S. Cl.
CPC ............. *A61N 1/403* (2013.01); *A61N 5/025* (2013.01); *A61N 5/04* (2013.01)

(58) Field of Classification Search
CPC ................................ A61N 5/025; A61N 1/403
See application file for complete search history.

(56) References Cited

U.S. PATENT DOCUMENTS

| 3,617,684 A | * | 11/1971 | Di Mino | ............. | H01C 17/265 |
|---|---|---|---|---|---|
| | | | | | 219/121.11 |
| 3,676,633 A | * | 7/1972 | Di Mino | ............. | H01C 17/265 |
| | | | | | 219/121.36 |

(Continued)

FOREIGN PATENT DOCUMENTS

| CN | 1657116 A | 8/2005 |
|---|---|---|
| EP | 2703042 | 3/2014 |

(Continued)

OTHER PUBLICATIONS

United Kingdom Patent Application No. GB1506851.3—United Kingdom Search Report dated Aug. 18, 2015.

(Continued)

*Primary Examiner* — Kaitlyn E Smith
(74) *Attorney, Agent, or Firm* — Renner, Otto, Boisselle & Sklar, LLP

(57) ABSTRACT

An apparatus and method for providing hyperthermia therapy to a living subject, in particular a human, animal or plant. The apparatus has contains a signal generator, a signal modulator and an emitter to enable the apparatus to provide hyperthermia treatment. Hyperthermia therapy may be provided to a living subject by generating a signal, selectably modulating the signal and delivering the signal to the target location on the living subject. It is possible to interrupt any further use of the apparatus after a predetermined period.

19 Claims, 14 Drawing Sheets

(56) References Cited

U.S. PATENT DOCUMENTS

| | | | |
|---|---|---|---|
| 4,667,677 A * | 5/1987 | Di Mino | A61N 1/32 607/71 |
| 4,719,919 A * | 1/1988 | Marchosky | A61F 7/00 606/27 |
| 5,190,037 A | 3/1993 | Di Mino et al. | |
| 5,983,141 A * | 11/1999 | Sluijter | A61N 1/403 607/100 |
| 6,066,164 A * | 5/2000 | Macher | A41D 19/01535 219/528 |
| 6,161,048 A * | 12/2000 | Sluijter | A61N 1/36021 607/100 |
| 6,246,912 B1 * | 6/2001 | Sluijter | A61N 1/36017 607/100 |
| RE40,279 E * | 4/2008 | Sluijter | 606/34 |
| 8,306,629 B2 * | 11/2012 | Mioduski | A61B 18/1233 607/100 |
| 8,690,748 B1 | 4/2014 | Fu | |
| 2002/0026226 A1 * | 2/2002 | Ein | A61F 7/007 607/108 |
| 2002/0077627 A1 * | 6/2002 | Johnson | A61B 18/1477 606/41 |
| 2003/0130711 A1 * | 7/2003 | Pearson | A61B 18/1477 607/101 |
| 2004/0111084 A1 | 6/2004 | Brett | |
| 2004/0230263 A1 | 11/2004 | Samulski | |
| 2005/0015125 A1 | 1/2005 | Mioduski et al. | |
| 2005/0251234 A1 | 11/2005 | Kanzius et al. | |
| 2005/0283148 A1 * | 12/2005 | Janssen | A61B 18/1477 606/34 |
| 2006/0161054 A1 | 7/2006 | Reuss et al. | |
| 2006/0190063 A1 | 8/2006 | Kanzius | |
| 2007/0093801 A1 * | 4/2007 | Behnke | A61B 18/1233 606/34 |
| 2007/0123961 A1 * | 5/2007 | Danek | A61B 18/1492 607/101 |
| 2007/0167999 A1 * | 7/2007 | Breden | A61N 5/06 607/88 |
| 2007/0249969 A1 * | 10/2007 | Shields, Jr. | A61N 7/00 601/2 |
| 2007/0250139 A1 * | 10/2007 | Kanzius | A61N 1/406 607/100 |
| 2007/0255269 A1 * | 11/2007 | Shin | A61B 18/1206 606/34 |
| 2008/0114428 A1 | 5/2008 | Trembly et al. | |
| 2009/0036938 A1 * | 2/2009 | Shipley | A61H 9/0078 607/2 |
| 2009/0254008 A1 * | 10/2009 | Shields, Jr. | A61N 7/00 601/3 |
| 2010/0049261 A1 * | 2/2010 | Bare | A61N 1/40 607/1 |
| 2010/0161010 A1 * | 6/2010 | Thomas | A61M 21/00 607/88 |
| 2011/0071371 A1 * | 3/2011 | Li | A61B 5/0059 600/310 |
| 2011/0092884 A1 | 4/2011 | Kang | |
| 2011/0245636 A1 * | 10/2011 | Li | A61B 5/02416 600/310 |
| 2011/0276113 A1 * | 11/2011 | Cybulski | A61B 18/042 607/101 |
| 2012/0065714 A1 * | 3/2012 | Szasz | A61B 18/1206 607/101 |
| 2013/0046357 A1 * | 2/2013 | Neev | A61N 5/022 607/45 |
| 2013/0317576 A1 * | 11/2013 | Rogers | A61F 7/007 607/99 |
| 2014/0065664 A1 | 3/2014 | Aknine | |
| 2014/0088487 A1 * | 3/2014 | Harris | A61M 5/14276 604/20 |
| 2014/0358189 A1 * | 12/2014 | Mashiach | A61N 1/0526 607/42 |
| 2015/0105701 A1 * | 4/2015 | Mayer | A61M 16/14 601/3 |
| 2015/0359478 A1 * | 12/2015 | Eyal | A61B 5/0095 600/437 |
| 2016/0030408 A1 * | 2/2016 | Levin | A61B 5/04001 514/330 |
| 2016/0380598 A1 * | 12/2016 | McLeod | H03F 1/26 600/509 |

FOREIGN PATENT DOCUMENTS

| | | |
|---|---|---|
| JP | 57157164 A | 9/1982 |
| JP | 2007-536016 A | 12/2007 |
| JP | 2012-515604 A | 7/2012 |

OTHER PUBLICATIONS

Patent Cooperation Treaty (PCT) International Search Report, dated Jan. 26, 2016.

Patent Cooperation Treaty (PCT) Written Opinion of the International Searching Authority (Korea), dated Jan. 25, 2016 (dated Jan. 26, 2016).

* cited by examiner

APPARATUS AND METHOD FOR PROVIDING HYPERTHERMIA THERAPY

CLAIM OF PRIORITY

This application is being filed as a non-provisional patent application under 35 U.S.C. § 111(a) and 37 CFR § 1.53(b). This application claims priority under 35 U.S.C. § 119(a) to United Kingdom patent application number P62760GB, filed on Apr. 22, 2015, and under 35 U.S.C. § 119(e) to U.S. provisional patent application Ser. No. 62/049,802 filed on Sep. 12, 2014, the contents of which are incorporated herein by reference in their entirety.

FIELD OF INVENTION

The present invention relates to an apparatus and method for providing hyperthermia therapy to a living subject, in particular a human, animal or plant.

BACKGROUND OF THE INVENTION

Hyperthermia therapy is a type of medical treatment in which body tissue is exposed to slightly higher temperatures to damage and kill cancer cells or to make cancer cells more sensitive to the effects of radiation and certain anti-cancer drugs. Local hyperthermia has shown to be effective when combined with chemotherapy or radiation therapy for cancers such as breast, cervical, prostate, head and neck, melanoma, soft-tissue sarcoma and rectal cancer, among others, in humans and in animals.

Hyperthermia therapy is sometimes delivered by means of enemy emitting devices designed to focus microwave or radio-frequency (RF) energy on the targeted area. The microwave or RF energy is delivered by placing an applicator or antenna in contact or close proximity with the subject being treated. Examples of such a device can be found, for example, in U.S. Patent Application Publication Nos. 2006/0265034 and 2014/0065664

One drawback of these devices is that the applicator antenna progressively degrades through use to the point where it can no longer serve its purpose as intended. A degraded antenna, in addition to being ineffective can also cause harm to a patient or to the energy emitting device it connects to. In addition, there is a general need in the art to improve devices and methods for providing hyperthermia therapy.

It is difficult, without careful record-keeping, to predict with any degree of precision when an antenna applicator is going to degrade to the point of non-functionality or when it will become hazardous to continue to use same. Even with careful record-keeping, a degraded antenna applicator may be mistakenly used since its appearance does not necessarily indicate its condition.

Accordingly there is a need in the art for an antenna applicator device for a hyperthermic therapy apparatus that automatically becomes disabled when it reaches its calculated maximum safe operation lifetime.

The present invention seeks to address these and other shortcomings encountered in the art.

SUMMARY OF THE INVENTION

In a first aspect of the invention, an apparatus for providing hyperthermia therapy to a living subject. The apparatus comprises a signal generator configured to generate a carrier signal, a signal modulator configured to selectably modulate the carrier signal with a modulating signal, and an emitter configured to deliver the modulated carrier signal to a target location on the living subject.

Whilst the apparatus may be merely suitable for providing hyperthermia therapy, in some embodiments the apparatus is specifically configured to do so. The carrier signal typically has a frequency in range of 6 mHZ to 250 mHZ. The operator or user of the apparatus may control the signal modulator such that they may select the modulating signal used to modulate the carrier signal. In particular they may select one or any number of frequencies to modulate the carrier signal, at any time prior to or during delivery of the therapy. Typically, the signal generator and signal modulator are comprised in a common enclosure whilst the emitter (which generally takes the form of an applicator mechanism or antenna) may be coupled to the signal generator and/or signal modulator via a lead, cable, or similar coupling mechanism able to propagate the modulated carrier wave.

The carrier signal may comprise a radio wave. The apparatus may generate a microwave radio frequency carrier signal of about 434 MHz, or any other frequency which is contained within the acceptable Industrial, Medical and Scientific (ISM) bands as authorised by numerous organisations on multiple continents of the world.

The generation of the carrier signal may be pulsed, and the signal generator may be further configured to selectively vary a pulse repetition rate of the pulsed carrier signal. The apparatus, through a microprocessor control system, may selectably vary a variable pulse repetition rate for the carrier signal that can range from but is not limited to half a second to 5000 on-off cycles per second. Advanced carrier signals of 40 kilohertz are also prototyped and useful for superpulsed 434 MHz carrier signals for physiological resonant applications.

The signal generator may be further configured to selectably vary duty cycle of the pulsed carrier signal. The apparatus, through the microprocessor control system, may be able to vary the duty cycle ratio of the turn-on time and the turn-off time within the mathematic division of the selected pulse repetition rate. The duty cycle ratio of carrier up time may be controllable and may vary from about 1% with a "Carrier On Time" and 99% with a "Carrier Off Time", and vice versa.

The modulation of the carrier signal may comprise modulating a frequency of the carrier signal. The modulating signal may comprise a frequency of between about 0.1 Hz and about 50 KHz. The modulating signal may comprise an audio signal. The apparatus, through the microprocessor control system, may apply audio onto the carrier signal in the form of frequency modulation. This frequency modulation through the imprint of audio information may range from audio information with a frequency of about 0.1 of a Hertz to over 50,000 Hertz. In one embodiment the modulating signal may comprise ultrasound.

The apparatus may apply stored audio protocols as modulations to the carrier signal. These audio protocols may include but are not be limited to single frequencies, multiple Simultaneously generated frequencies, and stored audio material. The selection of the desired audio protocol may be made by the user of the apparatus.

The apparatus may accept additional audio formats and protocols by both direct transfer to the apparatus (for example via a mass storage device), and/or by download with a remote master device or from the Internet or other network.

The apparatus may be used to enhance phase transitions in cell biology. The apparatus may be designed to deliver specific frequencies in order to stimulate specific biological functions by taking advantage of the association-induction theory, where radio and electrical fields affect at a distance biological water in tissues and cytoplasm.

The apparatus may deliver any of the resonant frequencies of the body parts being treated in order to match that body part's resonant frequency and take advantage of the resonant energy of the body part being treated. Thus, the apparatus may efficiently deliver energy to the target body part at relatively low power.

The apparatus may be used to enhance molecular/Brownian motion of water in protoplasm/cytoplasm of the living subject. This increase in energy delivered to the water in the tissues is capable of opening up neural microtubules and enhancing phase transitions in neural and other tissues.

Recent studies demonstrate the benefits of 10 and 50 Hz square waves in neurologic rehabilitation and enhanced nerve growth by the use at these frequencies. For example, reference is made to the following publications:

Coombe, D. R. (2002). CELLS, GELS AND THE ENGINES OF LIFE. Immunol Cell Biol, 80(5), 506-506.

Gabriel, S, Lau, R. W., &. Gabriel. C. (1996). The dielectric properties of biological tissues: III. Parametric models for the dielectric spectrum of tissues. Physics in Medicine and Biology, 41(11), 2271.

Trevors, J., & Pollack, G. (2012). Origin of microbial life hypothesis: a gel cytoplasm lacking a bilayer membrane, with infrared radiation producing exclusion zone (EZ) water, hydrogen as an energy source and thermosynthesis for bioenergetics. Biochimie, 94(1), 258-262.

Xun, S. (2011). Increased dielectric constant in the water treated by extremely low frequency electromagnetic field and its possible biological implication. Journal of Physics: Conference Series, 379(1) 012019.

Pollack., G. H., Cameron, I., and Wheatley, D., Water and the Cell. Springer, 2006.

Pollack, G. H. and Chin, W.-C. Phase Transitions in Cell Biology, Springer, 2008.

The device may deliver AM 10 Hz square waves, 50 Hz square waves, FM modulated sweeps from 5-13 Hz square waves, 10 Hz and Schumann frequency sweeps in order to specifically enhance neurological rehabilitation using a 434 MHz carrier wave through a multilayer applicator.

The apparatus may deliver low-frequency modulation of a 434 MHz carrier frequency in the 29-39 Hz range and more specifically 31.2 Hz) in order to enhance bone healing rates in fracture and post-surgical repairs.

The apparatus may deliver low-frequency AM modulation of a 434 MHz carrier frequency in the 22-27 Hz range in order to stimulate collagen for enhanced wound healing and skin toning.

The apparatus may deliver low-frequency AM modulation of a 434 MHz carrier frequency in the 4-13 Hz range in order to stimulate general abdominal organ resonant frequencies. 4-8 Hz stimulation of the kidneys may stimulate vasodilation and improve renal perfusion.

The apparatus may deliver low-frequency AM modulation of a 434 MHz carrier frequency in the 7.83-9 Hz range in order to warm, vasodilate improve hepatic and pancreatic function.

The apparatus may deliver low-frequency AM modulation of a 434 MHz carrier frequency in the 7.83-9 Hz range in order to warm, vasodilate and improve uterine function and diminish uterine spasms The apparatus may further comprise a thermal monitor configured to monitor a thermal state of the device. The apparatus may be configured to constantly monitor a thermal condition of the electronics of the apparatus. If at any time the apparatus is unable to monitor the thermal condition, or the thermal condition exceeds programmed nominal ranges, the apparatus may display a warning on the user interface, and may enter a shutdown protocol for safety. A dangerous thermal event detected by the thermal monitoring system may also cause the apparatus to communicate the event, to a remote master device.

The device may further comprise a tamper-proofing mechanism. The apparatus may operate an anti-tamper and anti-theft protocol. If required information is not entered on demand on to the apparatus, the apparatus may display a warning and may no longer operate until the remote master device is able to communicate with the apparatus to re-initialise the user's authority. Additionally, the apparatus may be able to determine whether the integrity of a container, box, or travel case in which the apparatus is contained has been compromised. Should the integrity of the enclosure have been compromised, the apparatus may display a warning that the operational microprocessor has shut down and that all operational source code has been deleted. This condition may only be reversed by allowing the apparatus to communicate with the remote master device.

The signal modulator may be further configured to vary the modulating signal modulating the carrier signal during provision of the hyperthermia therapy.

A frequency of the modulating signal may be selected according to a resonance frequency of a material at the target location. The apparatus may be configured to deliver frequencies that stimulate and activate the effects of tissue resonance in the body by accurately matching the frequency/frequencies of the input signal to these resonance frequencies. The apparatus may therefore warm tissues quickly and stimulate physiologic processes that are activated by these physiological resonant frequencies.

The apparatus may further comprise a light-emitting device configured to illuminate the target area during provision of the hyperthermia therapy, in one embodiment the apparatus may be fitted with a multipoint light-emitting diode system consisting of 470 nm light-emitting diodes. The combination of 470 nm light-emitting diodes together with a 434 MHz carrier wave may be used for infectious wounds and to enhance wound healing.

The apparatus may further comprise a thermal monitor configured to monitor a temperature of the living subject during delivery of the hyperthermia therapy. The thermal monitor may be incorporated in a garment worn by the living subject. In one embodiment, temperature probes may be woven into or attached to a wearable garment in order to monitor body surface temperature.

The apparatus may further comprise a usage monitor configured to monitor a usage parameter of the emitter, and an interruption device configured to automatically prevent further use of the emitter when the monitored usage parameter reaches a predetermined threshold. This may be a useful safety mechanism to prevent unwanted use of the emitter when the emitter has degraded to a point where further use may be dangerous to the living subject and/or detrimental to the apparatus.

The usage parameter may comprise a total time of use of the emitter or a number of on/off cycles of the emitter.

The emitter may comprise an applicator mechanism (such as an antenna) which may take many different forms and shapes. For example, the emitter may be in the form of a pad, a sleeve, a cast, an item of clothing, etc. The emitting portion of the emitter may be incorporated within a protective sheath, cover or case designed to be placed in contact with or in close proximity to the living subject. The emitter may be disposable following use.

The apparatus may further comprise a wireless communications device for communicating with a remote controller, and the apparatus may be configured to receive and act on instructions sent by the remote controller to the wireless communications device. The apparatus may be configured to communicate autonomously (for example at regular intervals) with the remote controller or remote master device. The mote master device may be located on the premises of company controlling or owning the apparatus, and may send commands to the apparatus to authorise the apparatus for use. Preferably, such communication contains no HIPPA or personal data. The apparatus may report its present location to the remote master device, its travel routes, the number and type of treatment protocols, and survey data feedback provided by either the patient (if human) or a clinical specialist. If it is found by the remote master device during a data share protocol that the apparatus is not in a location that is approved for that user, the apparatus may be remotely disabled by the remote master device. In addition, a message may appear on the user interface prompting the user or clinical specialist to contact the parent company. The apparatus may further comprise an Ethernet port.

The apparatus may be embodied in an item of furniture or clothing. The apparatus may be incorporated into a piece of furniture or clothing such that hyperthermia therapy may be delivered to a user when using the piece of furniture/clothing. For example, the apparatus may be incorporated into a couch, a chair, a blanket or a wetsuit. In such cases the emitter may be embodied in the form of therapeutic pads for stimulation of various body parts.

In a further aspect of the invention there is provided a method of providing hyperthermia therapy to a living subject. The method comprises generating a carrier signal, modulating the carrier signal with a modulating signal, and delivering the modulated carrier signal to a target location of the living subject.

In a further aspect of the invention, there is provided an apparatus for providing hyperthermia therapy to a living subject. The apparatus comprises an emitter configured to deliver a signal to a target location of the living subject, a usage monitor configured to monitor a usage parameter of the emitter, and an interruption device configured to automatically prevent further use of the emitter when the monitored usage parameter reaches a predetermined threshold.

The usage parameter may comprise a total time of use of the emitter or a number of on/off cycles of the emitter.

The emitter may be configured to be applied to a surface of the living subject.

The emitter may degrade through use.

Automatically preventing further use of the emitter may comprise automatically stopping power from being delivered to the emitter.

In a further aspect of the invention, there is provided a method of providing hyperthermia therapy to a living subject. The method comprises emitting a signal to a target location of the living subject, monitoring a usage parameter of the emitter, automatically preventing further use of the emitter when the monitored usage parameter reaches a predetermined threshold.

Further features of the invention are described below. As would be recognised by the skilled person, any of these features may be incorporated with any of the above embodiments.

The apparatus may be provided for use in a portable fashion, and may incorporate an openable case or similar enclosure for storing the apparatus and protecting it from the outside environment. The enclosure may include wheels for moving the apparatus and an extendable drag handle.

The apparatus may comprise a digital control system for carrying out various functions performed by the apparatus. The apparatus may include a multiple-platform microprocessor used to task and slave other sub-system controlled microprocessors to control the apparatus. Access to these various microprocessors may be achieved through a user interface, such as a touch screen.

The apparatus may comprise a Global Positioning System (GPS) for automatically locating the apparatus. The position data may be written to the microprocessor for further use. Auto-location of the apparatus may occur multiple times per day so that during relocation of the apparatus the location and track of travel can be ascertained when needed.

The apparatus may include an audio input jack for acceptance of an external audio signal to be impressed on the carrier signal and for storage in a memory of the apparatus.

The apparatus may also be configured to monitor a temperature of the target area of the living subject. For example, Thermo Eprom microprocessors and infrared forward-looking thermo-sensors may be employed in order to monitor thermal responses from subcutaneous tissue activity. An advanced flexible tape PCB thermo-sensing device may be coupled with the emitter for even field, and field encompassing temperature monitoring, via temperature probes allowing non-invasive granular temperature sensing.

The emitter (or applicator mechanism) may be formed and spread in many body-contouring ways in order to increase ergonomics. Disposable peel and stick thermo-sensors may be fashioned in order to more accurately monitor temperature around a specific body part being heated and treated by the apparatus. These non-invasive thermo-sensors may also be made to be invasive through their introduction into the body via laparoscopic, injection or minimally invasive surgical approaches. The temperature probes may be used during in vivo for advanced procedures such as oncology or long-term temperature monitoring systems left in situ.

The apparatus may be connected to an AC mains supply, and/or may include an on-board rechargeable battery source for limited DC field use. Should the apparatus be tampered with, detection of the tampering may cause a distress and location signal to be sent to the remote master device via cell, wireless or Ethernet. The distress signal may continue until the battery runs out or until deactivated by service personnel if the apparatus is connected to a power source.

The apparatus may include means for providing forced air cooling, such as a fan or pump for pumping coolant.

The apparatus may include a safety shutdown device, which may be user-activated via the user interface in the event of any type of problem. The shutdown device may be available as an extendable cord or wireless switch that the patient can push if there is discomfort felt by the patient at any time. The shutdown device can be removed or added as an accessory to the apparatus. The subject may also control an intensity of the therapy (for example via the shutdown device) to ensure comfort during the therapy.

The apparatus may be configured to change protocol parameters whilst in operation. Changes to the operational modalities can also be made whilst the apparatus is dormant and awaiting use.

The apparatus may include multiple emitters (applicators), each arranged to emit a respective modulated carrier signal. The emitters may be combined to provide increased levels of therapy. Clinical applications that the apparatus may be used for include but are not limited to neurological, musculoskeletal, oncological, rehabilitation, arthritis and other joint pain relief and warming, erectile dysfunction, sports medicine, sports enhancement, stem cell activation, collagen activation, wound healing, bone fracture repair and endocrine warming.

The apparatus may be used on its own or in combination with other drugs and medications. The apparatus may be used to deliver hyperthermia therapy in the context of any of the following: equine and bovine musculoskeletal and reproductive work; pancreatic inflammation/pain and pancreatic cancer/neoplasia; hepatic inflammation/pain and liver cancer/neoplasia; renal inflammation/pain and kidney cancer/neoplasia; splenic inflammation/pain and splenic cancer/neoplasia: small and large bowel inflammation/pain and small and large bowel cancer/neoplasia; cardiac inflammation/pain and cardiac cancer/neoplasia; pulmonary inflammation/pain and lung cancer/neoplasia; brain/skull inflammation/pain and brain/skull cancer/neoplasia; anal-rectal inflammation/pain and anal-rectal cancer/neoplasia; ocular inflammation/pain and ocular cancer/neoplasia; bone and cartilage inflammation/pain and bone and cartilage cancer/neoplasia; auditory structures and organ inflammation/pain and auditory structures and/or organ cancer/neoplasia; muscle inflammation/pain and muscular cancer/neoplasia; plantar/foot inflammation/pain and foot cancer/neoplasia; hand inflammation/pain and hand cancer/neoplasia; thyroid inflammation/pain and thyroid cancer/neoplasia; adrenal gland inflammation/pain and adrenal gland cancer/neoplasia; pituitary gland inflammation/pain and pituitary gland cancer/neoplasia; oral inflammation/pain and oral cancer/neoplasia; mammary gland inflammation/pain and mammary gland cancer/neoplasia; neck and chest wall inflammation/pain and neck and chest wall cancer/neoplasia; ovarian and uterine inflammation/pain and ovarian and uterine cancer/neoplasia; prostatic and testicular inflammation/pain and prostatic and testicular cancer/neoplasia The apparatus may be used as a standalone or in combination with other drugs and medications for increasing the body's metabolic rate by increasing temperature over key organs such as kidneys, liver, heart, spleen, etc.

The apparatus may be used as a standalone or in combination with other drugs and medications in order to stimulate the immune system by locally elevating the temperature over the thymus remnant and the heart/hilar lymph nodes, preferably for 30 minutes at 41 degrees Celsius and 15 minutes over each kidney. This locally elevated temperature over these major immune areas is capable of raising the metabolic rate over these organs as a function of the apparatus being used to provide hyperthermia therapy to such target locations. The increase in temperature and the raising of the basal metabolic rate over these organs stimulates the immune system directly.

The apparatus may be used as a standalone or in combination with other drugs and medications for the treatment of renal disease as an electronic form of forced dieresis. By raising the temperature of one or both kidneys, the apparatus may increase renal function and three more blood flow to the kidneys and increase renal function. This is beneficial in the management of renal disease both in its acute and chronic phases.

The apparatus may be used to heat kidneys before dialysis therapy in order to increase the efficiency of dialysis and decrease the time it takes to filter the kidneys on a dialysis machine. The apparatus may therefore be used to accelerate dialysis therapy time.

The apparatus may be configured to stimulate tissues with a range of resonant frequencies between about 0.1 Hz and about 1.618 Hz. This may be used for the stimulation of pluripotent stem cells and the activation of these cells into tissue-specific stem cell lines such as heart, neuro, bone, liver, kidney, etc.

The apparatus, through the use of ELF and increased temperature, may be used as a non-invasive means of stem cell donor site activation. This activation may allow for stem cell migration, via circulation, to a recipient target site.

The apparatus, through the use of ELF and increased temperature, may be used as a non-invasive means of stem cell recipient site preparation and activation. This recipient site activation may allow for migratory stem cells to be adopted at the recipient site.

The apparatus may be configured to stimulate tissues with a range of resonant frequencies between about 4 Hz to about 13 Hz. This may be used for the stimulation of general organs and body parts and for the gentle warming of these tissues.

The apparatus may be configured to stimulate tissues with a range of resonant frequencies between about 9 Hz to about 11 Hz. 10 Hz is used specifically for the rehabilitation of connective tissues and especially nerves. The use of the apparatus has been demonstrated to rapidly rehabilitate and turn on previously damaged neurologic tissues. The apparatus may use Extremely Low Frequencies (ELF) to enhance neuro-genesis in damaged neuro tissue.

The apparatus may be configured to stimulate tissues with a range of resonant frequencies between about 21 Hz and about 27 Hz, for the rehabilitation of collagen and skin for use in beauty and spa applications.

The apparatus may be configured to stimulate tissues with a range of resonant frequencies between about 30 Hz to about 39 Hz. In particular, 31.2 Hz may be used for the rehabilitation of fractures bone healing and osteoporosis.

The apparatus may be configured to stimulate tissues with a range of resonant frequencies between about 89 Hz and about 120 Hz. In particular, 108 Hz may be used for the reduction of edema.

The apparatus may be configured to stimulate issues with a range of resonant frequencies between about 300 Hz to about 500 Hz, and upwards of 40,000 Hz for the treatment of pain and other neurological conditions.

A plurality of audio frequencies and audio wave shapes may be used to modulate the carrier signal, for stimulation of neurological rehabilitation as well as bone healing and re-growth.

The apparatus may be used to promote phase transitions of water from bulk water H2O into "EZ" water $H_3O_2$, a liquid crystal, and back again. The energy of the RF signal imparts energy into the body's water which can be used to increase the potential energy and increase molecular motion of the cellular and non-cellular body water. This increase in energy is used by the body's water to create structured "EZ" water and to separate waters charges into positive and negative charges along hydrophilic surfaces. These enhanced phase transitions encourage the rapid rehabilitation seen in neurological cases using the apparatus.

The apparatus may be used to decrease and/or dissolve various forms of calcifications in the body, both at a micro level as in the case of dissolving Ca blockages at damaged nerve tissue or glands, as well as a way to dissolve and diminish calcifications in joints, tendons and ligaments.

Various rhythmic and dysrhythmic tones and/or chords (used as the modulating signal) may be used by the apparatus to efficiently dissolve calcifications over time. The apparatus, through the use of ELF and increased temperature, may be used as a non-invasive means of dissolving calcified accumulations and crystallizations in soft tissue.

The apparatus n ay be used to electromagnetically warm drugs in the body to promote the activation of the drugs (such as Thermodox by Centrum), or iron oxide nanoparticles in the use hyperthermia for oncology.

The apparatus may be used in combination with Carboplatin or Cisplatin for the use of loco-regional oncological applications in order to deliver targeted immune therapy to cancers amenable to this therapy.

The apparatus may be used for the loco-regional treatment of mast cell tumours and melanoma in combination with Carboplatin, blue scorpion venom, and targeted immune therapy.

The apparatus may be used to heat bone to increase the plasma state of the bone and make it more visible to ultrasound. This may electronically extend the use of ultrasound in bone scanning by first heating up the hone prior to scanning with ultrasound, thus making the inside of the bone visible with ultrasound.

Similarly, the apparatus may be used to raise the temperature of anatomical regions prior to imaging with an MRI apparatus. Any heated region presents an electronic contrast medium for MRI due to the hyperexcitation and increased temperature of the heated area.

In one embodiment, the apparatus may be used to pulse a sequenced 10 Hz square wave down the path of a nerve. The signal is propagated along the nerve route such as from skull to foot or skull to arm.

With appropriate reduction in the power, the apparatus may be used as an electro-acupuncture stimulator. The apparatus may be used to directly stimulate any acupuncture point on the body of man or animal, or over acupuncture needles. Peel and stick applicator mechanisms may be used when connected to the apparatus to deliver the RF energy to the target acupuncture point. As an alternative treatment protocol, the emitter may comprise a lens for focusing the modulated carrier wave. Peel and stick printed resonant or chiral pattern resonant lens applicator mechanisms may be placed over a desired acupuncture area to be treated, in order to act as a 'microwave lens' and focus more energy to the desired acupuncture area.

These microwave lenses may be made to become active at different tunable resonant frequencies as determined by the touch screen user interface in the desired frequency ranges.

Still with reduced power in mind, the apparatus may be used in the treatment of arthritis and bone fractures, transcranial stimulation and rehabilitation for a variety of neurological conditions such as trauma, dementia, Alzheimer's, stroke, neoplasia, glioma, depression, pineal gland transcranial stimulation, cerebellar stimulation in epilepsy, anti-seizure transcranial RF stimulation, anti-tremor therapy, tinnitus therapy, and deep auditory stimulation, amongst others.

By tuning the modulation signal to the appropriate signal, the apparatus may be used as a repellent against marine predators. This embodiment has particular use when the apparatus is incorporated into a wetsuit or similar garment for use in water.

The emitter may be coated with a metamaterial such as graphene, carbon fiber, sapphire dust paste, emerald dust paste, ruby dust paste, and carbon nanotubes.

The apparatus may be used as a part of a diagnostic test for urethral reflux syndrome of children. In one embodiment, the bladder is warmed to 41 degrees C. and one or more temperatures sensors are placed over the kidneys to monitor renal temperature rise. A rise in renal temperature will signify that urine is refluxing from the bladder sending warm urine up to the kidney. This process would constitute a positive, non-invasive test for determining urethral reflux syndrome in infants.

The apparatus can be operated to automatically sense the self-resonant range of target materials in the living subject. In this automatic tuning mode, the apparatus may analyse signal return loss as a function of target location.

DESCRIPTION OF INVENTION

The present invention seeks to provide an unproved apparatus and method for providing hyperthermia therapy to a living subject. Whilst various embodiments of the invention are described below, the invention is not limited to these embodiments, and variations of these embodiments may well full within the scope of the invention which is to be limited only by the appended claims.

Figure 1:
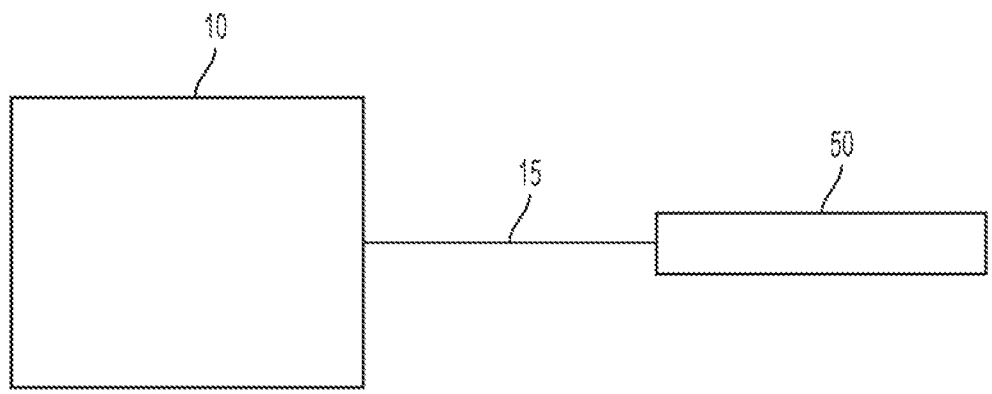
FIG. 1 is a schematic diagram of a hyperthermia delivery system in accordance with an embodiment of the invention.

FIG. 1 is a schematic diagram of a hyperthermia delivery system in accordance with an embodiment of the invention. The hyperthermia delivery system comprises an apparatus 10 configured to generate and modulate a carrier wave. Apparatus 10 is shown in more detail in FIGS. 2 and 3, and described in more detail below. The hyperthermia delivery system further comprises an applicator mechanism 40 connected to apparatus 10 by suitable means 15 (such as a coaxial cable). Applicator mechanism 40 is configured to be positioned on or in close proximity to a living subject, for efficient delivery of the modulated carrier wave generated by apparatus 10 and transmitted to applicator mechanism 40 via means 15. Applicator mechanism 40 is shown in more detail in FIGS. 4-14 and described in more detail below.

Figure 2:
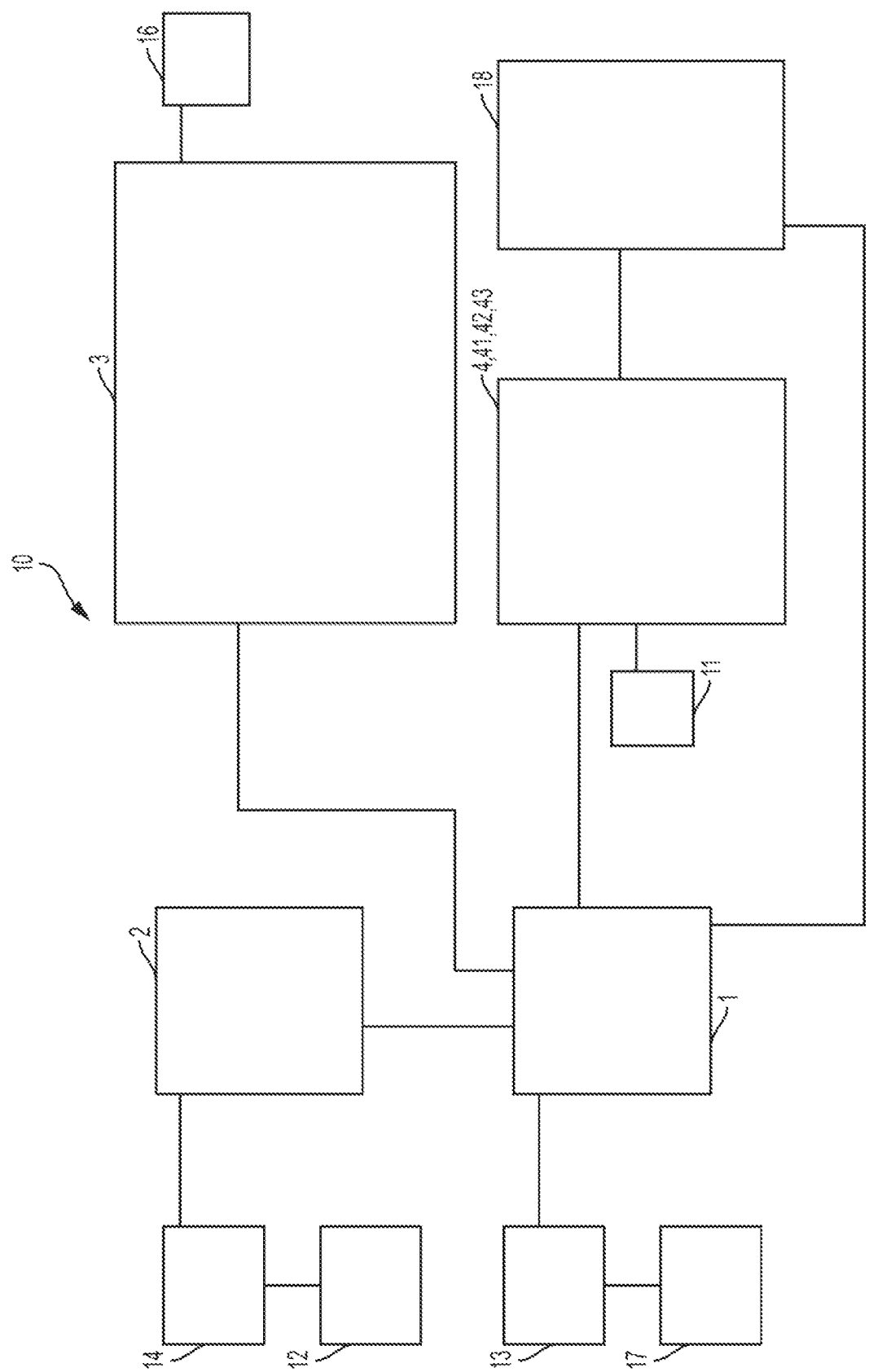
FIG. 2 is a schematic diagram of components of an apparatus in accordance with an embodiment of the invention.

FIG. 2 is a schematic representation of apparatus 10 configured to generate and modulate a carrier wave for hyperthermia therapy, in accordance with an of the invention. Apparatus 10 comprises comprising four primary circuit cards or circuit modules 1, 2, 3, 4.

Card 1 is an interconnect card that contains various individual control circuits that are proprietary to the operation of apparatus 10. Card 1 is the interconnect point for all peripherals related to apparatus 10. Interconnection to Card 1 is made via multi-conductor cable connectors with multiple connective contacts. Card 1 is modular and is easily replaced for serviceability and/or troubleshooting. Card 1 incorporates both surface-mount electronic components as well as through-hole electronic components, and multiple circuit inter-connective plug and socket assemblies. Test points are placed prudently throughout Card 1 for testing and troubleshooting. Card 1 comprises a multilayer printed circuit board designed to eliminate or minimise where possible any additional hand-wiring or connections that may cause reliability problems with apparatus 10. Card 1 may be connected to a thermos jack connect 13, which may be connected to a thermos sensor package 17.

Apparatus 10 further comprises Card 2 which is a power supply mains card. This power supply contains circuits that are proprietary to the operation of apparatus 10. Various DC voltage potentials are created on Card 2 and interconnection to Card 1 is made through multiple conductor cable. Command, control and power are routed to Card 2 through the multiple conductor cables with removable contacts attached to Card 1. Card 2 is modular and is easily replaced for serviceability and/or troubleshooting. AC mains level potential 12 connects directly to Card 2 and bypasses the interconnect Card 1 for safety considerations. AC mains voltage potential 12 is conveyed through a specially selected combination radio frequency interference filter, a circuit breaker/power switch 14, and a universal disconnectable cordage connection. Apparatus 10 may also operate on universal AC voltage mains.

Card 2 creates the necessary DC voltage that is required to operate apparatus 10. The power supplies used on Card 2 are modular in format and both Card 2 itself and the individual power supplies may be readily replaced for testing and service if needed by the user, in particular a qualified or authorised service technician. Multiple DC voltages are created on Card 2 and are used to operate and/or segregate the DC mains voltages required for use by the various circuits of apparatus 10. Test points are prudently located on Card 2 for testing and troubleshooting.

Apparatus 10 further comprises Card 3 (which may be referred to herein as RF deck) which is a radio frequency generating and amplification module. Card 3 is a proprietary module that incorporates RF components required to cause apparatus 10 to create a 434 MHz carrier wave. Card 3 is interconnected to the master interconnect card (Card 1) via multiple conductor cable connections with multiple connective removable contacts attached to Card 1. Command, control and power are routed to Card 3 through the multiple conductor cables. Card 3 is modular and is easily replaced for serviceability and/or troubleshooting. Radio frequency energy that is created by Card 3 is coupled to an output connection of apparatus 10 via a coaxial cable and a conventional Type TNC female panel jack 16. Jack 16 is custom-selected for low power losses, integrity of the impedance match to the applicator mechanism (not shown), mechanical integrity, and ease of use when attaching different applicator mechanisms.

Apparatus 10 further comprises Card 4 which is a digital control interface card. Card 4 connects with the master interconnect card (Card 1) via multiple conductor cable connections with multiple connective removable contacts attached to Card 1. Command, control and power are routed to Card 4 through the multiple conductor cables. Card 4 is modular and is easily replaced for serviceability and/or troubleshooting. Card 4 also directly connects to an apparatus touch screen control panel 18 that is mounted on the outside surface of apparatus 10. This direct connection is made to eliminate reliability issues with the touch screen control surface. Card 4 also has a direct connection to an environmentally stable Universal Serial Bus (USB) connection 11 on the outer surface of apparatus 10. USB connection 11 is provided for local interconnection of the digital control card (Card 4) to a servicing technician, for repair of apparatus 10, updates, upgrades, or general troubleshooting.

Although not shown, apparatus 10 is cooled by a plurality of motor-driven cooling devices, such as fans or coolant pumps. Heat is removed from the apparatus's sub-systems and is imparted to an air flow column within apparatus 10 which is then exchanged with the ambient air both within and from without apparatus 10 to ensure a stable operational environment.

Apparatus 10 further includes an embedded Global Positioning System 41 installed within a travel case housing apparatus 10 on Card 4. The GPS system works in conjunction with digital microprocessor 42, contained on Card 4, in order to periodically write a message to the memory of digital microprocessor 42 identifying the position/location of apparatus 10.

Apparatus 10 further includes an embedded cellular modem 43 installed within the case, also on Card 4. This cellular modem 43 system works in conjunction with digital microprocessor 42 to perform many functions. The modem 43 periodically connects to the parent company to report a number of accumulated bits of data that may comprise for example the position/location of apparatus 10, the types of treatments used by the user, the quantity of the treatments, and other related data as accumulated by digital microprocessor 42.

In a particular embodiment of the invention, apparatus 10 is housed within a water-resistant and ruggedized travel case with carry handles, drag handles and wheels. This water resistant travel case is the functional conveyance shell as well as the container for apparatus 10. The case is weather and dirt resistant and offers protection to apparatus 10 as well as storage options for mains voltage power cables, applicator mechanisms, etc.

Figure 3:
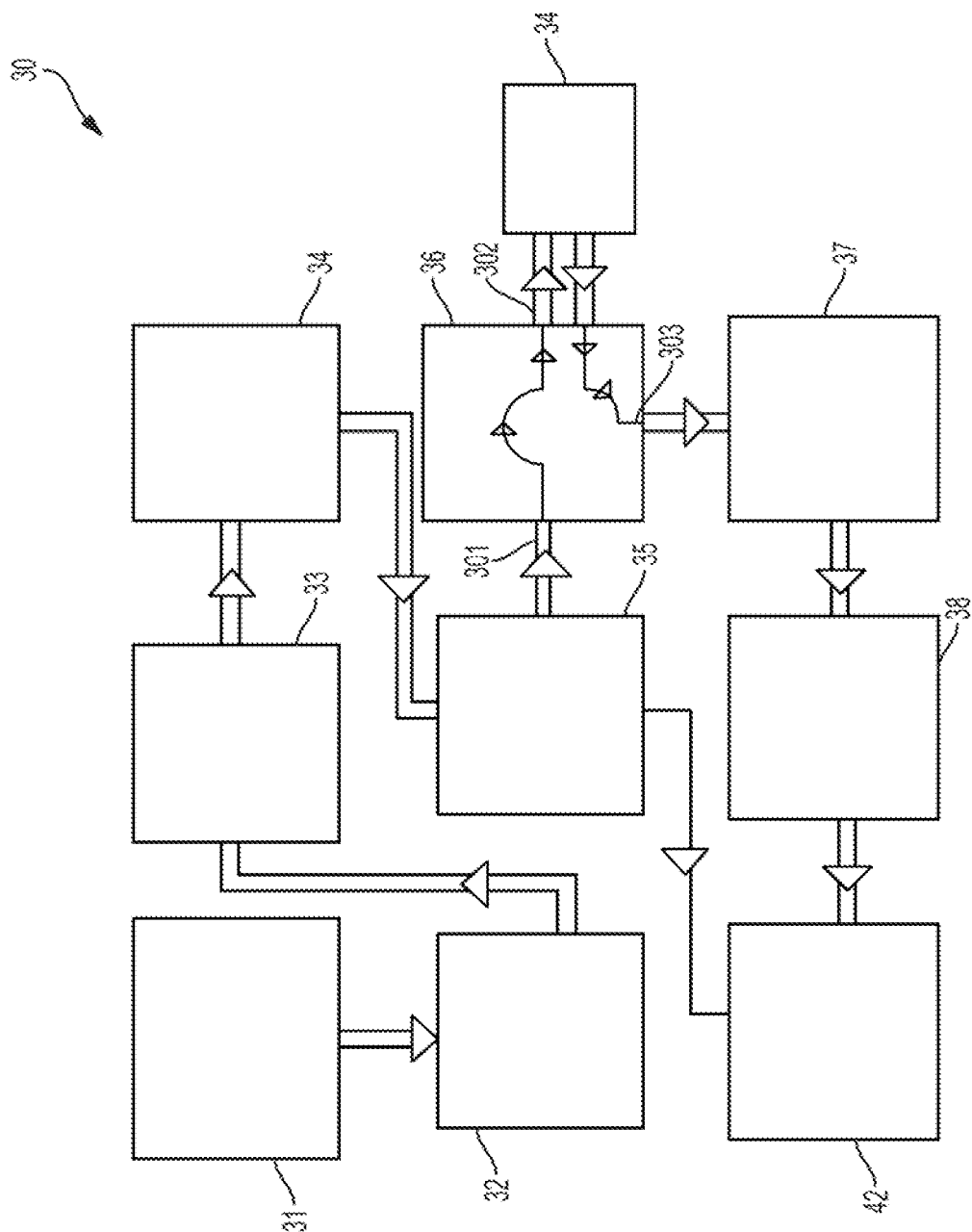
FIG. 3 is a schematic diagram of components of the RF deck of FIG. 2.

Now turning to FIG. 3, the components of RF deck 30, or Card 3, and their interconnection is shown in more detail.

RF deck 30 comprises exciter 31 configured to create a stable frequency source for the 434 MHz RF carrier wave. This spectrally pure RF carrier wave is self-referenced internally to exciter 31 for frequency stability within the requirements of the Industrial, Medical, and Scientific band requirements of the various communications authorities of the world.

Exciter 31 also provides the Frequency Modulation (FM) portion of the therapeutic treatment. The FM audio information is intermixed with the carrier wave to produce a complex wave form output from exciter 31. The output of exciter 31 is continuous with respect to the RF modulation signal and is as commanded by the digital controller card (Card 4). The audio information may be generated from a plurality of audio cards within apparatus 10. The audio cards are polyphonic digitally controlled devices that are capable of being commanded to generate a range of modulating signals. These signals are commanded by digital microprocessor 42 (comprised in Card 4) to vary in (amongst others) amplitude, frequency, waveform shape, and singular or polyphonic modes. The output of the audio from these cards is summed or added together and is applied to exciter 31 to modulate the carrier wave. The exciter 31 outputs its signal into an attenuator 32 to modify the power of the signal.

RF deck 30 further comprises a pre-amplifier 33 configured to accept the complex signal from exciter 22 after it has passed through the attenuator 32 and boost the signal level to a therapeutic level as required for the intended treatment program as selected by the user. A power gain of a variable nature is designated by the user as selected on touch screen control panel 18. The treatment protocol may be selected as having an output power level from zero to multiples of tens of Watts, to be delivered to the applicator mechanism through a low loss Type TNC panel mounted connection and a low loss type of coaxial cable.

The pre-amplifier 33 transmits the signal to the final power amplifier 34. The final power amplifier 34 is commanded by digital microprocessor 41 to perform a number of functions related to the desired therapeutic action of apparatus 10. Final power amplifier 33 is commanded to either operate or sit quiescent at maximum or minimum output power. The output power can be commanded to vary in level in a continuously variable range from zero output to maximum output. Final power amplifier 33 can be commanded to vary the duty cycle ration of 'turn on' time as related to 'turn off' time as a mathematic function of operations per second. This variability in duty cycle ratio is continuously variable in 1% shifts ranging from one percent 'on time' and 99% 'off time' to a converse 99% 'on time' and a 1% 'off time'. An additional function of final power amplifier 34 is to vary the number of turn-on operations per second as commanded by digital microprocessor 41. In a particular embodiment, the range of pulse repetition rates or pulse operations per second is variable from half an operation per second (0.5 Hz) to greater than 5000 operations per second (5 KHz). This plurality of combinations of variable output power, variable pulse repetitions per second, and variable pulse width ratio duty cycles, creates a wide range of therapeutic and palliative care treatment options for the living subject, as selected by the user.

RF deck 30 further comprises directional coupler 35. Directional coupler 35 senses the output power of final power amplifier 34 and sends this amplitude-related information to digital microprocessor 41. This is a check and balance safety mechanism to ensure that final power amplifier 34 is operating in accordance with the therapeutic treatment protocol that was selected for use. Directional coupler 35 also senses any unused RE energy from the applicator mechanism. Any unused energy is expressed as a loss in the term VSWR. VSWR is a ratio of the forward energy and any reflected or unused energy. The expression of perfection is 1:1.00. Digression from perfection toward the quantity 1:3.00 is not a desired operational condition. Energy that is unused or 'reflected back' toward apparatus 10 by the applicator mechanism can cause damage to final power amplifier 34.

RF deck 30 further comprises isolator/circulator 36 configured to allow a radio frequency signal to enter it and exit it. Isolator/circulator 36 functions as a one-way safety route with the function of protecting final power amplifier 34 from electrical damage due to a misapplication of the applicator mechanism or failure of the applicator mechanism. Isolator/circulator 36 comprises three RF connections associated with it. RF energy from final power amplifier 34, via directional coupler 35, enters isolator/circulator 36 on port 301. An action similar to a traffic circus occurs in a clockwise round-about motion. This motion allows the applied RF energy from port 301 to exit isolator/circulator 36 with minimal losses through port 302. In a perfect condition substantially 100% of the energy that exits port 302 is consumed by the applicator mechanism (not shown) which is connected through a carrier wave output connection 39 and imparted to the living subject. As this condition of perfection is a rare occurrence, this unused energy expressed as VSWR (Voltage To Standing Wave Ratio—see below) is reflected backward toward isolator/circulator 36. This reflected energy re-enters isolator/circulator 36 on port 302 and in a traffic circus clockwise motion exits isolator/circulator 36 on port 303 (hence the terminology isolator/circulator 36). Port 303 is a unidirectional portal that is only capable of allowing the energy that is reflected into port 302 to leave isolator/circulator 36 via port 303. The energy that is expelled from port 303 is shunted toward a resistive apparatus known as reject attenuator 37.

Reject attenuator 37 is a two-port device with an input and an output. Reject attenuator 37 lowers (i.e. attenuates) any level of power introduced to the input port of reject attenuator 37 and allows a lower value image of the power to leave the output port of reject attenuator 37. The RF signal is converted to a Direct Current (DC) format by a small electronic circuit. The resulting DC energy is also fed toward digital microprocessor 42 as an alternate means of measuring or extrapolating the value of the efficiency of the coupling of the 434 MHz carrier wave signal to the living subject. This resultant DC value may be used to drive a display of the efficiency of the coupling of the applicator mechanism to the living subject, and may be located on touch screen digital display 18.

As a safety feature in digital microprocessor 42, when the VSWR approaches 1:1.30, the amplifier output power that is delivered to the applicator mechanism is reduced to a level that is both safe for the living subject and safe for the electrical integrity of pre-amplifier 33 and final power amplifier 34. As an aid to the user, there is an efficiency indication on touch screen control panel 18. If the applicator mechanism is improperly applied to the living subject, the efficiency indication may turn for example from green to yellow, and if the efficiency of the coupling continues to degrade, the efficiency indication may turn from yellow to red.

RF deck 30 further comprises reject load attenuator 38. Reject load attenuator 38 is a two-port device which accepts AC or DC signals, or a combination of both, and lowers the amount of energy in a logarithmic rate expressed typically in Decibels (dB). Reject load attenuator 38 is used as a safety mechanism to supply a DC voltage level to digital microprocessor 42 in order to develop an indication of the efficiency of the applicator mechanism in coupling the carrier wave to the living subject. In order to carry out its attenuation function, heat is developed and must be dissipated. This heat dissipation is accomplished by attaching reject load attenuator 38 to a heat sink.

Figure 4:
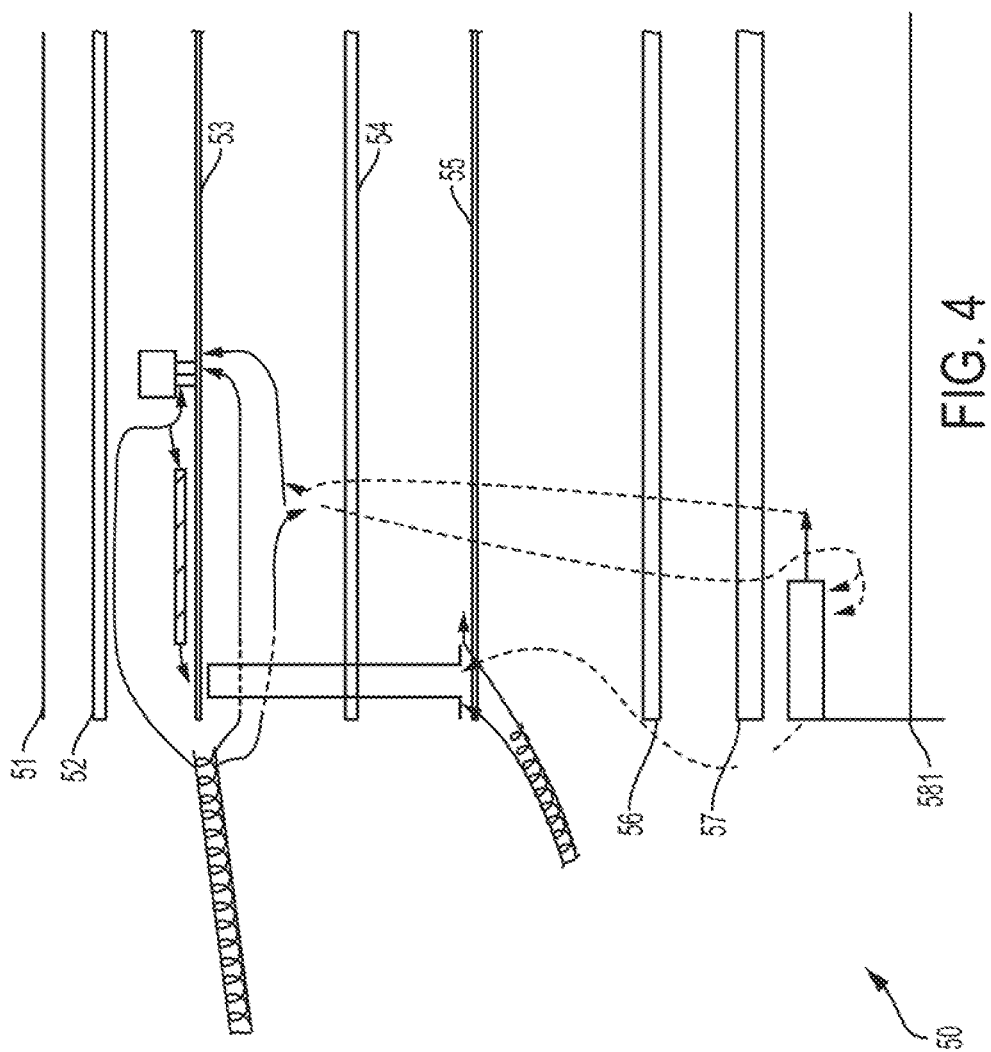
FIG. 4 is a schematic diagram of an applicator mechanism in accordance with an embodiment of the invention.

Now turning to FIG. 4, there is shown an applicator mechanism 50 in accordance with an embodiment of the invention. Applicator mechanism 50 may be connected to apparatus 10 via suitable means (e.g. via a disconnectable coaxial cable), and is configured to deliver the modulated carrier wave to the living subject so as to provide hyperthermia therapy.

Applicator mechanism 50 comprises a multilayer structure including in the following order: front outer cover 51, first dielectric layer 52, slot antenna 53, second dielectric layer 54, microstrip antenna 55, third dielectric layer 66, backing 57, and rear outer cover 58. Details of each layer are shown in FIGS. 5-14. The different layers interact in several ways.

Figure 5:
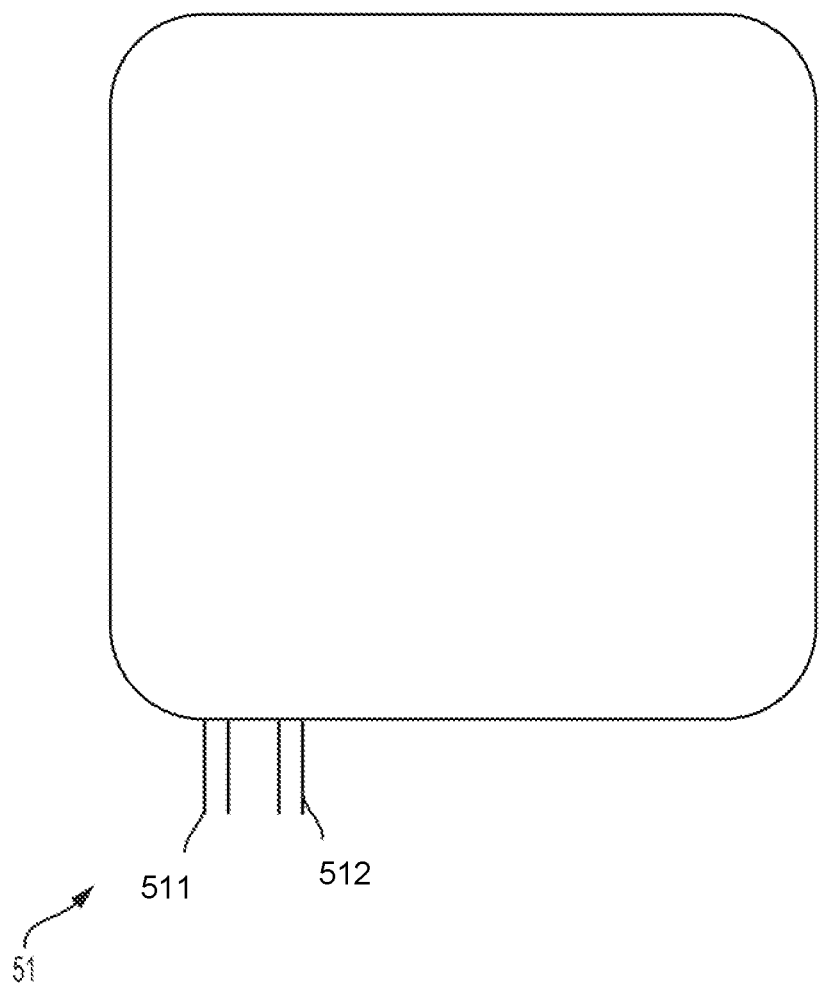
FIG. 5 shows the front outer cover of an applicator mechanism in accordance with an embodiment of the invention.

FIG. 5 is a view of front outer cover 51. Front outer cover is designed to be applied at in proximity to the target area of the living subject undergoing hyperthermia therapy. The front outer cover can be made from a polyurethane fiber or any other flexible material. In this embodiment, it includes two ports, a coaxial cable port 511 and a temperature sensor cable port 512.

Figure 6:
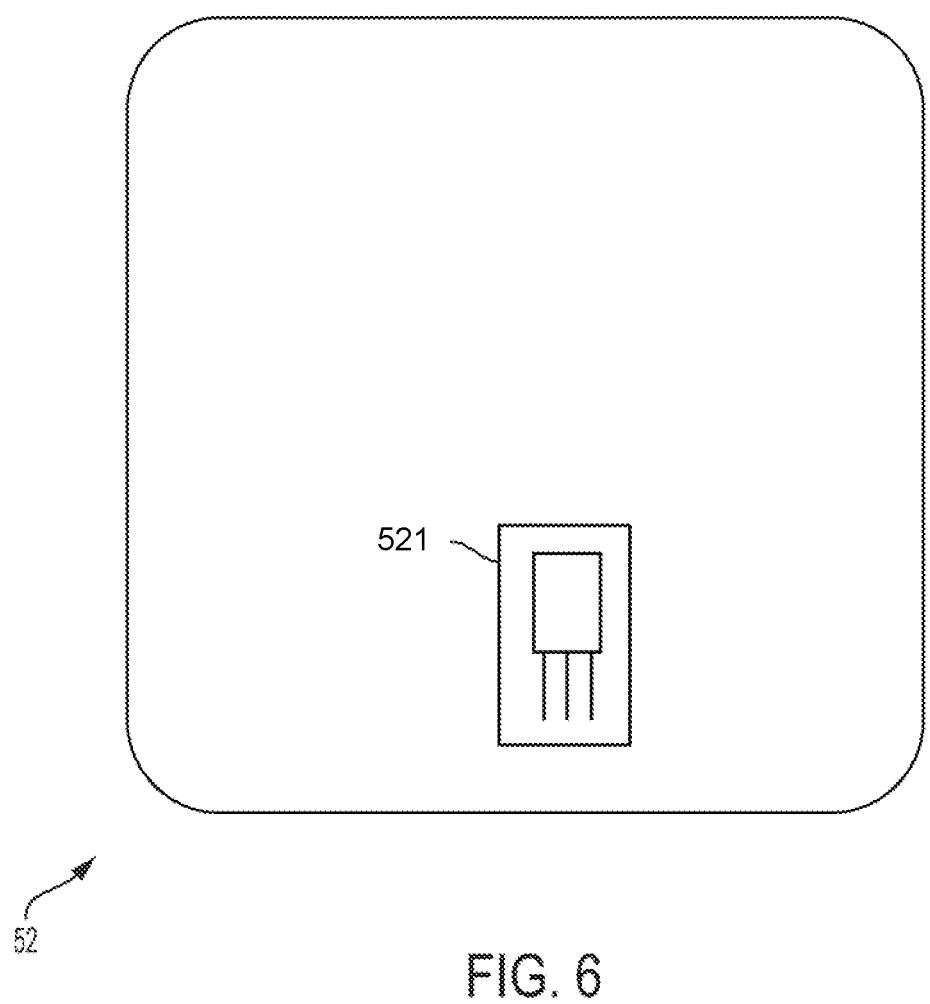
FIG. 6 shows the first dielectric layer of an applicator mechanism in accordance with an embodiment of the invention.

FIG. 6 is a view of first dielectric layer 52 comprises an opening 521 for receiving a temperature sensor with built-in microchip therethrough. The thermometer allows temperature readings of the living subject to be taken during delivery of the therapy. The first dielectric layer 52 can be made from silicone or any other insulative material and can have a thickness of about 1.5 mm. In one embodiment, the dielectric constant of dielectric layer 52 is approximately 2.9.

Figure 7:
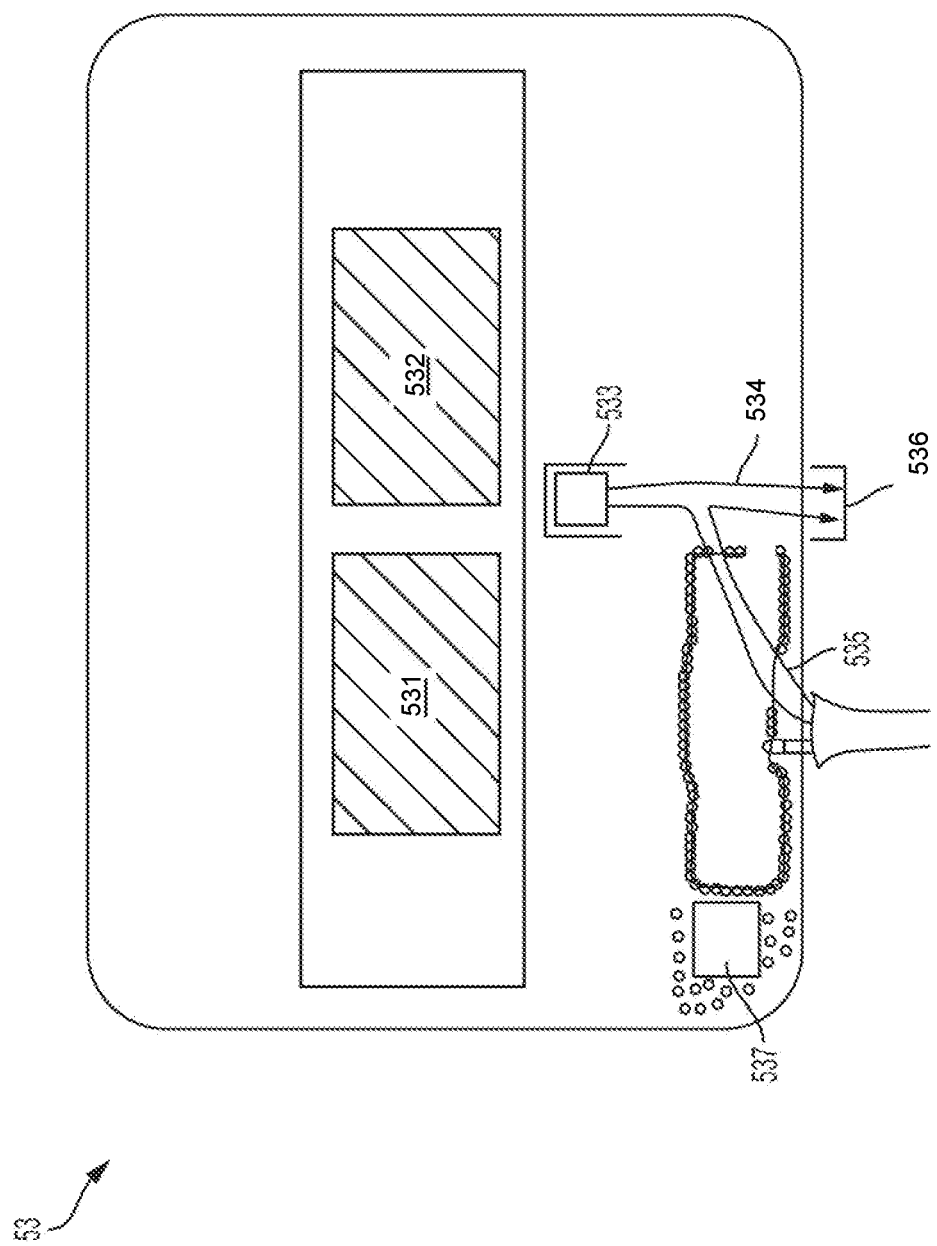
FIG. 7 shows the top side of the slot antenna of an applicator mechanism in accordance with an embodiment of the invention.
Figure 8:
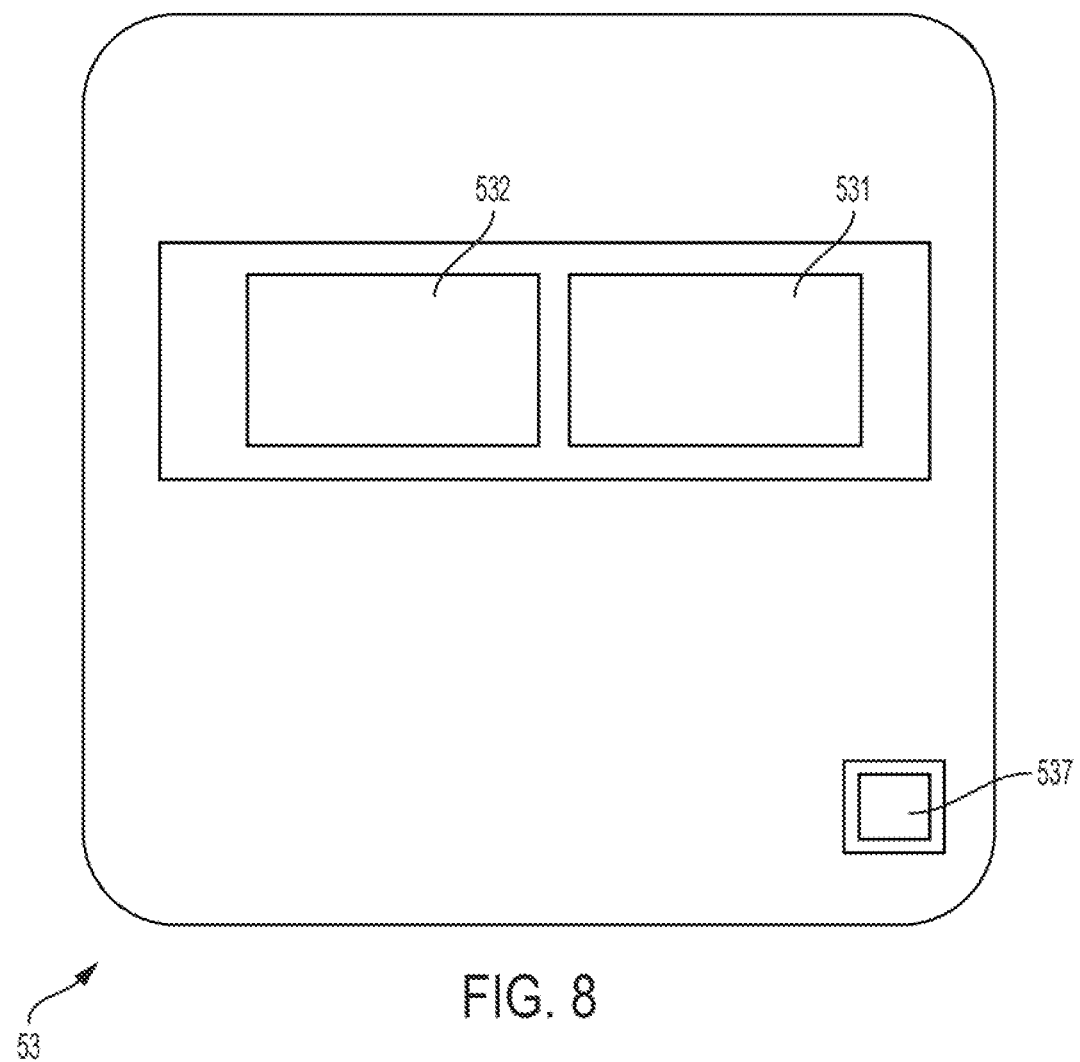
FIG. 8 shows the bottom side of the slot antenna of an applicator mechanism in accordance with an embodiment of the invention.

FIG. 7 is a view of slot antenna 53 that is underneath the first dielectric layer 52. When applicator mechanism 50 is connected to apparatus 10, the modulated carrier wave generated by apparatus 10 is transmitted to slot antenna 53 for delivery of the modulated carrier wave to the living subject. Slot antenna 53 comprises two microwave lenses 531 532 for focusing the modulated carrier wave emitted from slot antenna 53. The two microwave lenses 531 532 do not touch each other or the slot antenna 53. Slot antenna 53 can be made from a flat flex circuit material with approximately 0.5 mm thickness. Slot antenna 53 further comprises temperature IC 533, a first connector 534 between the temperature IC and the microcontroller 581, a second connector 535 between temperature IC 533 and an external power and data source tot shown), a metal support plate 536, and a slot 537 for the ground weld to go through. FIG. 8 is a view of the other side of the slot antenna 53 that borders the second dielectric layer 54.

Figure 9:
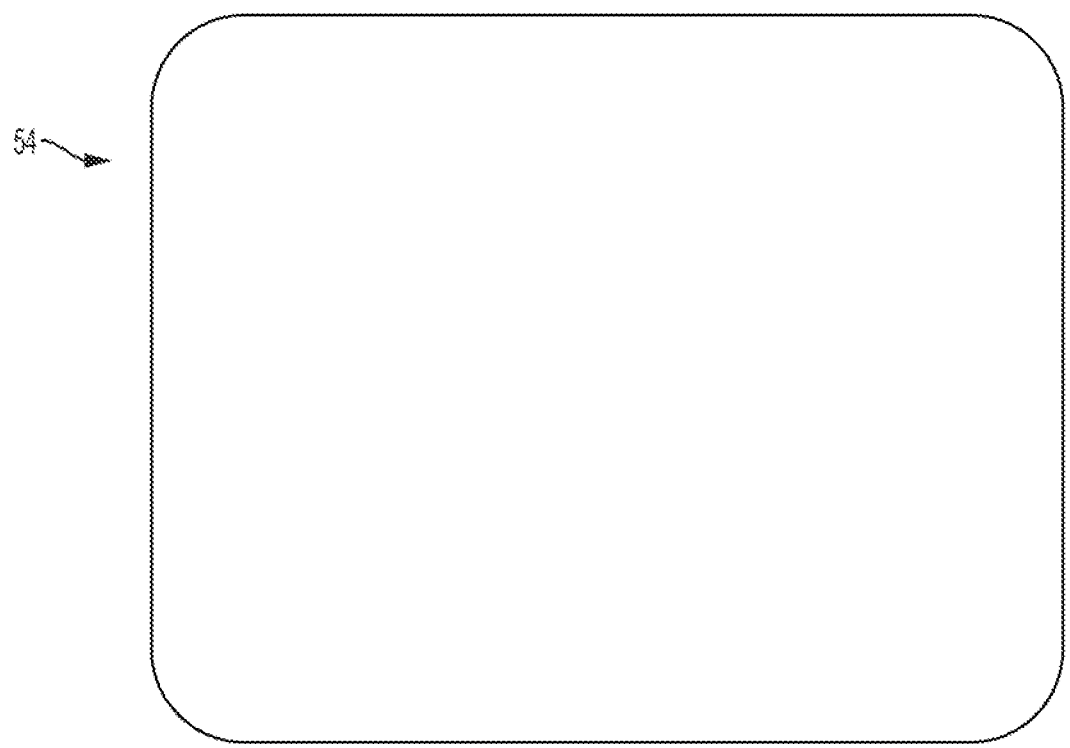
FIG. 9 shows the second dielectric layer of an applicator mechanism in accordance with an embodiment of the invention.

FIG. 9 shows the second dielectric layer 54. In conjunction with first dielectric layer 52, it serves to electrically isolate slot antenna 53 from microstrip antenna 55. The second dielectric layer 54 can be made from silicone or any other insulative material with a dialectic constant of 2.9. It can have a thickness of about 1.5 mm.

Figure 10:
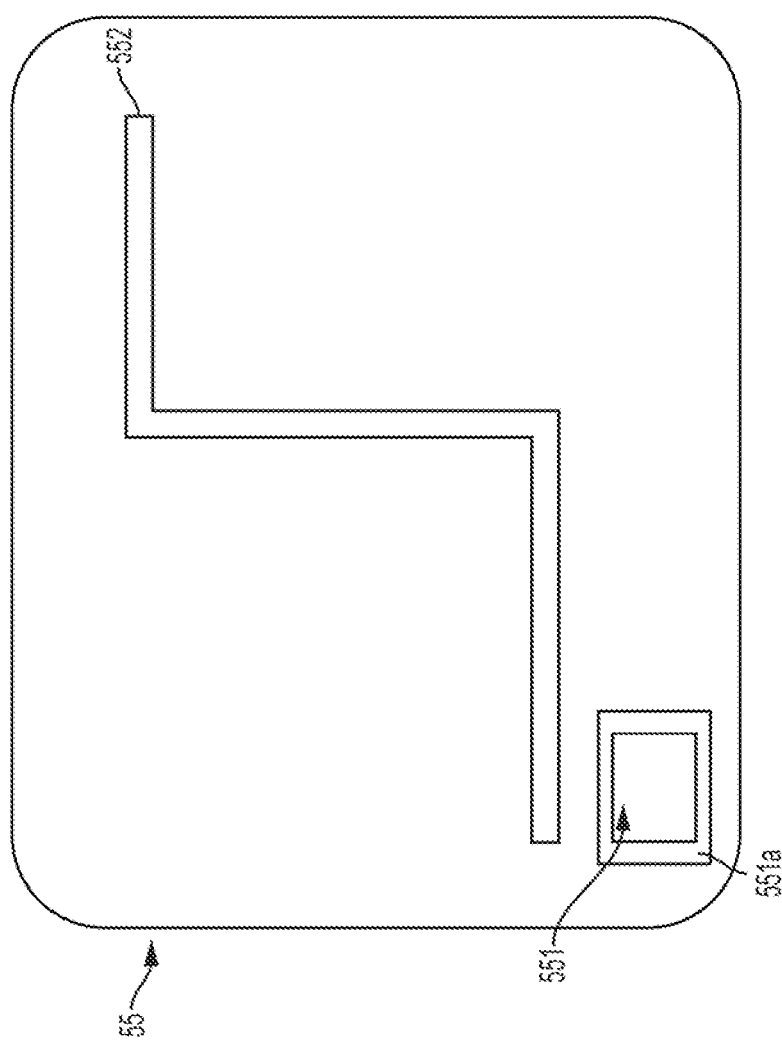
FIG. 10 shows the top side of the microstrip antenna of an applicator mechanism in accordance with an embodiment of the invention.
Figure 11:
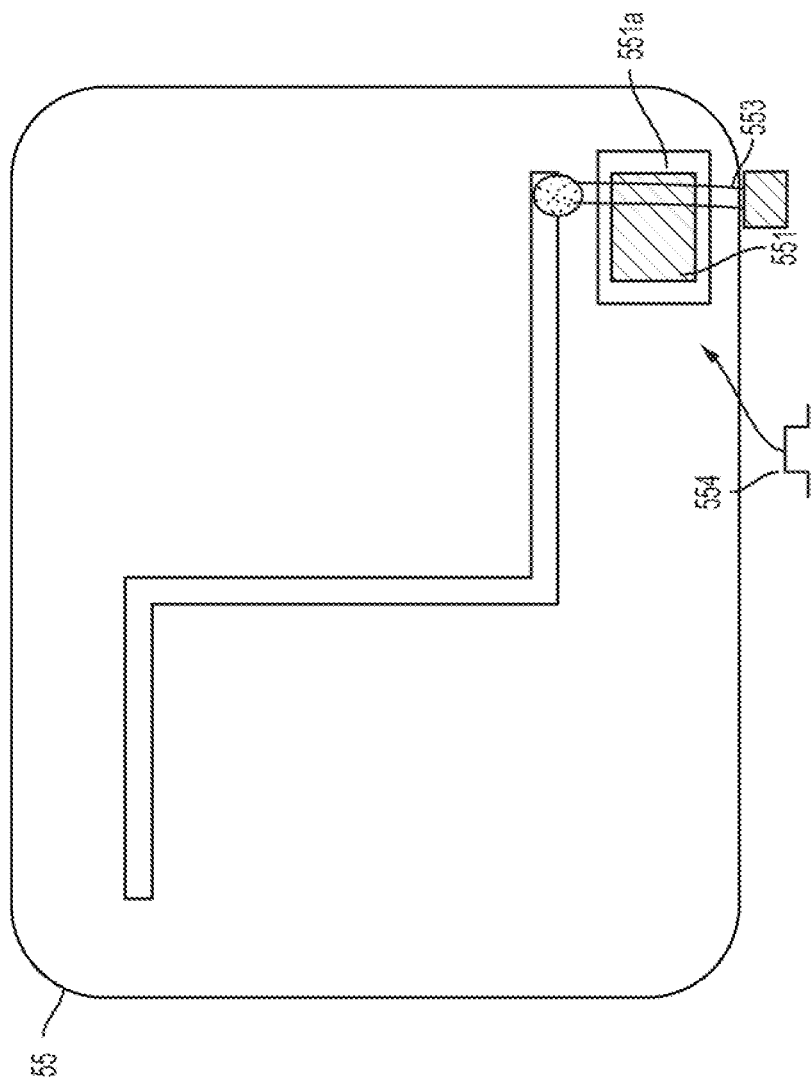
FIG. 11 shows the bottom side of the microstrip antenna of an applicator mechanism in accordance with an embodiment of the invention.

FIG. 10 shows the side of microstrip antenna 55 that faces the second dielectric layer 54. The microstrip antenna includes a slot 551 for a ground wire to pass through and connect to microcontroller 581. The slot 551 is surrounded by a ground rim 551*a*. It also has a cut out 552 in a z-like shape. The corner of the microstrip antenna 55 is bonded to the other layers with epoxy. FIG. 11 shows the other side of the microstrip antenna 55 that borders the third dielectric layer 56, this is the welded side of the microstrip antenna 55. A copper extension clip for around is connected to slot 551 through to slot antenna 53. The microstrip antenna 55 further comprises a copper extension clip 553 and a copper connection clip 554.

Figure 12:
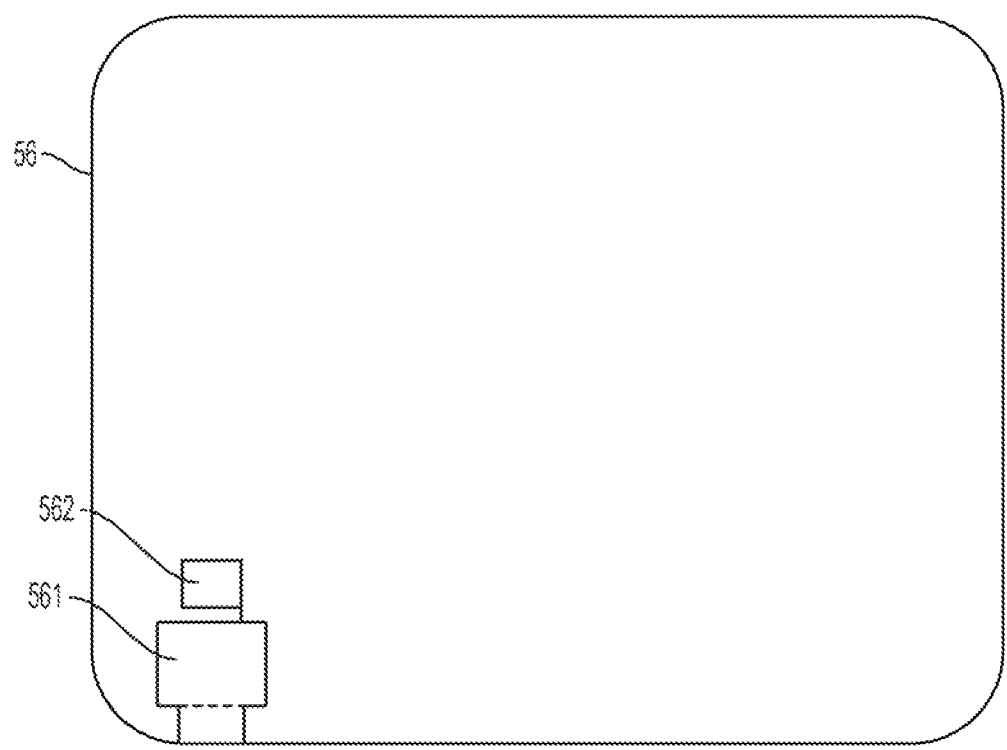
FIG. 12 shows the third dielectric layer of an applicator mechanism in accordance with an embodiment of the invention.

FIG. 12 shows the third dielectric layer 56. The third dielectric layer 54 can be made from silicone or any other insulative material with a dialectic constant of 2.9. It can have a thickness of about 1.5 mm. There is a slot 561 for the coaxial lead and ground to connect the microstrip antenna 55 to the microcontroller 581. There is a smaller slot 562 located above the first slot 561 for the lead.

Figure 13:
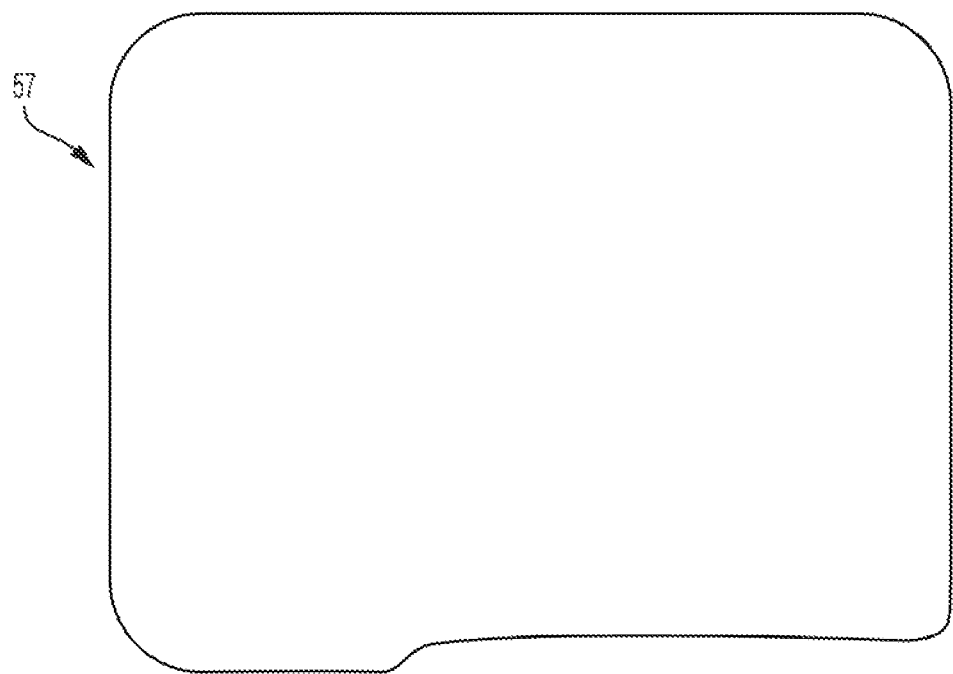
FIG. 13 shows the backing of an applicator mechanism in accordance with an embodiment of the invention.

FIG. 13 shows the backing 57. Backing 57 can be made from a material similar to a wetsuit such as neoprene. The material has a preferred dielectric constant of 20.1. The backing 57 is not rectangular in that the bottom left portion, approximately 40%, is longer, approximately 9%, than the bottom right. This is to provide extra shielding for cable ground.

Figure 14:
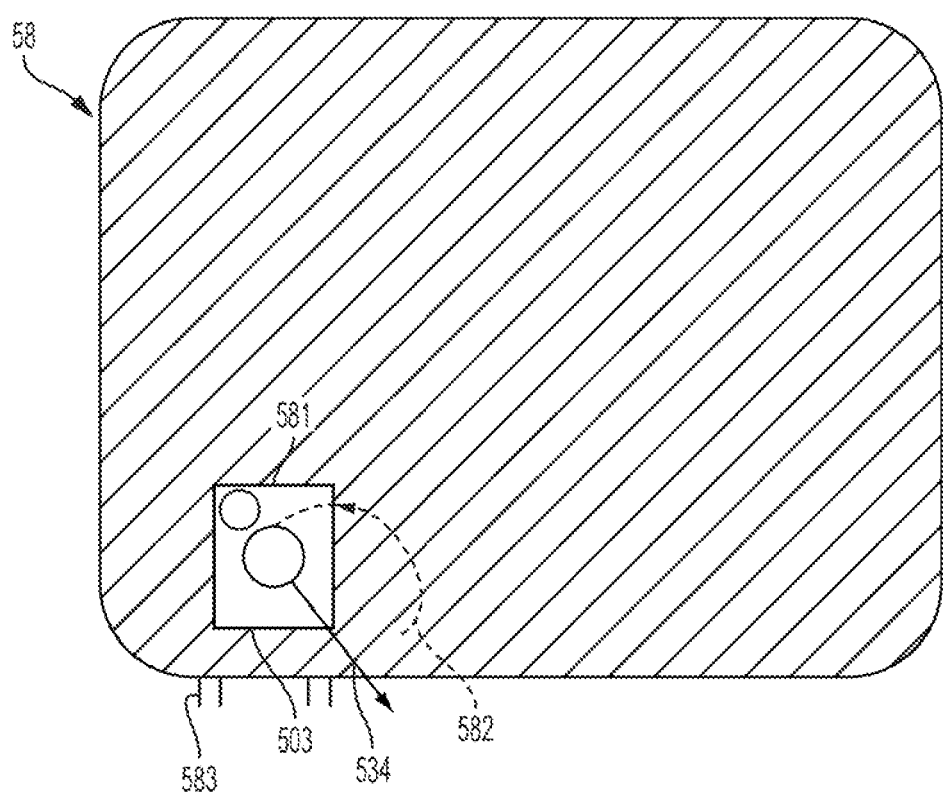
FIG. 14 shows the rear outer cover of an applicator mechanism in accordance with an embodiment of the invention.

FIG. 14 shows the rear of the outer casing 58. The outer casing has a microprocessor 581 attached. The microprocessor 581 may have three cables attached, a power in 582, a power out 534 to temperature IC, and a ground 583. All of the layers are sewn to close over the antenna assembly.

Applicator mechanism 50 includes a circuit that automatically disables slot antenna 53 one its useful life has been reached. Applicator mechanism 50 incorporates an energy interruption circuit (not shown) that controls the flow of energizing current drawn into and through slot antenna 53. The energy interruption circuit is activated through a microchip that calculates the extent of use of slot antenna 53 and permanently interrupts power to slot antenna 53 once a maximum use has been reached.

The microchip can measure the total time of use for slot antenna 53 by measuring the actual time of use for slot antenna 53 every time it is used and adding the time to a permanent counter built into, or programmed, into the microchip circuitry. Once the accumulated use time measured by the permanent counter reaches a pre-set limit, the energy interruption circuit is activated and slot antenna 53 is permanently disabled. Alternatively, the microchip can simply measure the number of on/off cycles for slot antenna 53 and, once a pre-set threshold limit of cycles is reached, the energy interruption circuit is activated and slot antenna 53 is permanently disabled. Other methods of measuring the useful life of the antenna can easily be envisioned by persons of ordinary skill in the art and incorporated into the logic of the referenced microchip.

Once slot antenna 53 has been disabled, the microchip circuitry can optionally generate an audible or visible signal to the operator to indicate that slot antenna 53 has exceeded its useful life and should be changed. Also optionally, the microchip can provide visible cues to the operator as the end of life approaches. For example, the operator may be shown a countdown or display of remaining lifetime or operating cycles for the device. Alternatively, the operator may simply be shown different coloured lights, or a certain number of lights to indicate how much time, or how many cycles remain in slot antenna 53.

Whilst the invention has been described in connection with specific embodiments, it is to be understood that the invention is not limited to these embodiments, and that alterations, modifications, and variations of these embodiments may be carried out by the skilled person without departing from the scope of the invention.

The invention claimed is:

1. An apparatus for providing hyperthermia therapy to a living subject, comprising:
   a signal generator configured to generate a carrier signal;

a signal modulator configured to selectably modulate the carrier signal with a modulating signal comprising an audio protocol including multiple simultaneously-generated audio signals, wherein the audio signals vary in frequency and waveform shape; and an emitter configured to deliver the modulated carrier signal to a target location on the living subject.

2. The apparatus of claim 1, wherein the carrier signal comprises a radio frequency carrier signal.

3. The apparatus of claim 1, wherein the carrier signal is a pulsed carrier signal.

4. The apparatus of claim 3, wherein the signal generator is further configured to selectively vary a pulse repetition rate of the pulsed carrier signal.

5. The apparatus of claim 3, wherein the signal generator is further configured to selectably vary a duty cycle of the pulsed carrier signal.

6. The apparatus of claim 1, wherein the modulation of the carrier signal comprises modulating a frequency of the carrier signal.

7. The apparatus of claim 1, wherein the modulating signal comprises frequencies of between about 0.1 Hz and about 50 KHz.

8. The apparatus of claim 1, wherein the signal modulator is further configured to vary the modulating signal modulating the carrier signal during provision of the hyperthermia therapy.

9. The apparatus of claim 1, wherein the living subject comprises a human, an animal or a plant.

10. The apparatus of claim 1, wherein frequencies of the modulating signal are selected according to a resonance frequency of a material of the target location.

11. The apparatus of claim 1, further comprising:

a usage monitor configured to monitor a usage parameter of the emitter; and an interruption device configured to automatically prevent further use of the emitter when the monitored usage parameter reaches a predetermined threshold.

12. The apparatus of claim 11, wherein the usage parameter comprises a total time of use of the emitter.

13. The apparatus of claim 11, wherein the usage parameter comprises a number of on/off cycles of the emitter.

14. The apparatus of claim 1, wherein the emitter comprises an applicator antenna.

15. The apparatus of claim 1, wherein the emitter is configured to be applied to a surface of the living subject.

16. The apparatus of claim 1, further comprising:

a wireless communications device for communicating with a remote controller, and wherein the apparatus is configured to receive and act on instructions sent by the remote controller to the wireless communications device.

17. The apparatus of claim 1, wherein the apparatus is an item of furniture such that hyperthermia therapy is delivered to the living subject when using the item of furniture.

18. The apparatus of claim 1, wherein the apparatus is an item of clothing, such that hyperthermia therapy is delivered to the living subject when wearing the item of clothing.

19. A method of providing hyperthermia therapy to a living subject, comprising:

generating a carrier signal;

selectably modulating the carrier signal with a modulating signal comprising an audio protocol including multiple simultaneously-generated audio signals, wherein the audio signals vary in frequency and waveform shape; and delivering the modulated carrier signal to a target location on the living subject.

* * * * *